(12) United States Patent
Campbell-Lee et al.

(10) Patent No.: US 11,872,296 B2
(45) Date of Patent: Jan. 16, 2024

(54) PRESERVATION COMPOSITIONS

(71) Applicant: Conopco, Inc., Englewood Cliffs, NJ (US)

(72) Inventors: Stuart Campbell-Lee, Wirral (GB); Rupak Mitra, Bangalore (IN); Thomas Richard Pointon, Warrington (GB); Ian Peter Stott, Wirral (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 90 days.

(21) Appl. No.: 17/056,592

(22) PCT Filed: May 20, 2019

(86) PCT No.: PCT/EP2019/062983
§ 371 (c)(1),
(2) Date: Nov. 18, 2020

(87) PCT Pub. No.: WO2019/233757
PCT Pub. Date: Dec. 12, 2019

(65) Prior Publication Data
US 2021/0205194 A1    Jul. 8, 2021

(30) Foreign Application Priority Data
Jun. 4, 2018 (EP) .................... 18175793

(51) Int. Cl.
A61K 8/362 (2006.01)
A61K 8/34 (2006.01)
A61Q 5/00 (2006.01)

(52) U.S. Cl.
CPC .............. *A61K 8/362* (2013.01); *A61K 8/347* (2013.01); *A61Q 5/00* (2013.01); *A61K 2800/524* (2013.01); *A61K 2800/74* (2013.01)

(58) Field of Classification Search
None
See application file for complete search history.

(56) References Cited

U.S. PATENT DOCUMENTS

| 3,448,132 | A | 6/1969 | Griebstein |
| 4,201,765 | A * | 5/1980 | Sichak ............... A61Q 17/005 514/699 |
| 5,580,849 | A | 12/1996 | Dyet et al. |
| 7,074,747 | B1 | 11/2006 | Lukenbach et al. |
| 8,778,314 | B2 | 7/2014 | Jones et al. |
| 9,326,924 | B1 | 5/2016 | Fourre et al. |
| 2008/0063618 | A1 | 3/2008 | Johnson et al. |
| 2012/0101135 | A1 | 4/2012 | Klug |
| 2012/0329874 | A1 | 12/2012 | Piva et al. |
| 2014/0311515 | A1 | 10/2014 | Barne et al. |
| 2016/0000094 | A1 | 1/2016 | Modak et al. |
| 2016/0060660 | A1 | 3/2016 | Hiller et al. |
| 2017/0151165 | A1 | 6/2017 | Scheunemann et al. |
| 2017/0360663 | A1 | 12/2017 | Schulze Zur Wiesche et al. |

FOREIGN PATENT DOCUMENTS

| BR | 102017003313 | 10/2018 |
| CN | 1366874 | 9/2002 |
| CN | 103998011 | 8/2014 |
| CN | 104078093 | 10/2014 |
| CN | 104152300 | 11/2014 |
| CN | 105133035 | 12/2015 |
| CN | 105228449 | 1/2016 |
| CN | 105296995 | 2/2016 |
| CN | 105457059 | 4/2016 |
| CN | 104116734 | 5/2016 |
| CN | 106459121 | 2/2017 |
| CN | 106565986 | 4/2017 |
| CN | 107189771 | 9/2017 |
| CN | 107519516 | 12/2017 |
| CN | 107937150 | 4/2018 |
| DE | 102017101868 | 9/2017 |
| DE | 202017001430 | 9/2017 |
| EP | 0853941 | 7/1998 |
| EP | 1082906 | 3/2001 |
| EP | 1433464 | 6/2004 |
| EP | 2807925 | 12/2014 |
| EP | 2320860 | 10/2017 |
| FR | 2877576 | 5/2006 |
| JP | 10109906 | 4/1998 |
| JP | 2001226205 | 8/2001 |
| JP | 2010239872 | 10/2010 |
| JP | 2018048104 | 3/2018 |
| WO | WO9405758 | 3/1994 |
| WO | WO9849257 | 11/1998 |
| WO | WO0061107 | 10/2000 |
| WO | WO2007084607 | 7/2007 |
| WO | WO2009019255 | 2/2009 |

(Continued)

OTHER PUBLICATIONS

IPRP2 in PCTEP2020070905.; Jul. 8, 2021.
Rybicki et al,; Molecular tracers preserved in Lower Jurassic "Blanowice brown coals" from southern POland at the onset of colaification: Organic geochemical and petrological characteristcs; Organic Geochemistry; 2016; pp. 77-92; 102.
4-Oxovaleric acid,; Surfactant.top; Aug. 26, 2021; pp. 1-4, https://www.surfactant.top/en/saa/?type=detail&id=7524.
Anti-Dandruff (Coal Tar) Topical: Uses, Side Effects, Interactions, Pictures, Warnings and Dosing; WebMD; 2017; pp. 1-4 (URL:https://web. archive,org/web/20170802013524/https:/).

(Continued)

*Primary Examiner* — Nicole P Babson
(74) *Attorney, Agent, or Firm* — Foley & Lardner LLP

(57) ABSTRACT

A preservation system comprising: i. itaconic acid or salt thereof and ii. an aromatic alcohol selected from the group consisting of ethylvanillin, eugenol, thymol, P-hydroxybenzaldehyde, 4n butyl phenol, P-hydroxyacetophenone, vanillin, salicylic acid or salt thereof, o-cymen-5-ol, carvacrol and mixtures thereof.

11 Claims, No Drawings

(56) References Cited

FOREIGN PATENT DOCUMENTS

| WO | WO2010018385 | 2/2010 | | |
|---|---|---|---|---|
| WO | WO2011092325 | 8/2011 | | |
| WO | WO2012135282 | 10/2012 | | |
| WO | WO2014161988 | 10/2014 | | |
| WO | WO-2015022033 A1 * | 2/2015 | ............. | A01N 25/02 |
| WO | WO2015197377 | 12/2015 | | |
| WO | WO2018092075 | 5/2018 | | |

OTHER PUBLICATIONS

Search Report and Written Opinion in EP18175856, dated Jul. 6, 2018.
Search Report and Written Opinion in EP18175825, dated Aug. 22, 2018; European Patent Office (EPO).
Search Report and Written Opinion in EP18175850, dated Mar. 1, 2019.
Liquid Detergent for Sensitive Skin; Liquid Detergent; Nov. 1, 2015; pp. 1-3.
Fortifying Shampoo; Fortifying Shampoo; Apr. 1, 2018; pp. 1-2.
Color-Depositing Conditioner; Color-Depositing Conditioner; 2018, pp. 1-3.
Search Report and Written Opinion in EP18175857, dated Jan. 3, 2019.
Mintel; Database GNPD Minte; Conditioner; 2016, pp. 1-3; XP2787014.
Mintel; Database GNPD Mintel ; Intense repairing conditioner; 2018, pp. 1-3; XP2787075.
Mintel; Database GNPD Mintel; Step-3 Conditioner; 2017, pp. 1-4; XP2787076.
Search report and Written Opinion in EP18175793, dated Jan. 8, 2019.
GNPD Mintel; GNPD Mintel; Shampoo Sunsilk Deeply; Jan. 2009; pp. 1-2 (also as XP002786946).
Advanced Repairing Shampoo; Database GNPD Mintel; 2018; pp. 1-2 (also as XP002786947).
Search Report and Written Opinion in EP18209554, dated May 21, 2019.
Search Report and Written Opinion in EP18209554; 21-May 2019; Att docket No. C7980EP; .
Search Report and Written Opinion in PCTEP2019062973, dated Jun. 25, 2019.
Search Report and Written Opinion in PCTEP2019062963, dated Jul. 5, 2019.
Search Report and Written Opinion in PCTEP2019062983, dated Jul. 8, 2019.
Search Report and Written Opinion in PCTEP2019062974, dated Jul. 8, 2019.
Search Report and Writtion Nopinion for PCTEP2019062962, dated Aug. 2, 2019.
Search Report and Written Opinion in EP, dated Aug. 29, 2019.
Search Report and Written Opinion in EP19189592, dated Oct. 18, 2019.
Somayeh Ghahari ; Phytochemical screening and antimicrobial activities of the constituents isolated from Koelreuteria paniculata leaves; XP55625821 Natural Product Research; Oct. 2, 2015; pp. 1865-1869; vol. 29, No. 19.
Nykaafrontendteam; Dhathri Dheedhi Anti-Dandruff for removing dandruff naturally herbal shampoo; XP055626744 URL:https://www.nykaa.com/dhathri-dheedhi-anti-dandruff-for-removing-dandruff-naturally-herbal-shampoo-100ml/p/417720; Jun. 18, 2019; whole document.
Pan Chun-Xiu ; Investigation on the Macromolucuilar Network Structure of Xianfeng Lignite by a New Two-Step Depolymerisation; Fuel, IPC Science & Technology Press; Dec. 8, 2012; pp. 49-53; vol. 109.
Search Report and Written Opinion in EP19189595; dated Oct. 18, 2019.
Luan Harding H et al; Food Fight : Role of Itaconate and Other Metabolites in Antimicrobial Defense; Sep. 13, 2016; pp. 379-387; vol. 24 No. 3.
Search Report and Written Opinion in PCT EP2019 081382, dated Jan. 21, 2020.
Partial Search Report and Provisional Written Opinion in PCTEP2019081362, dated Jan. 21, 2020.
Search Report and Written Opinion in PCTEP2019081362, dated Mar. 16, 2020.
Search Report and Written Opinion inPCTEP2020070904, dated Oct. 20, 2020.
Chouhan, S. et al.; Antimicrobial Activity of Some Essential Oils—Present Status and Future Perspectives; Medicines; 2017; 21 pages; 4(58).

* cited by examiner

PRESERVATION COMPOSITIONS

CROSS-REFERENCE TO RELATED APPLICATIONS

This application is a U.S. National Stage Application under 35 U.S.C. § 371 of International Application No. PCT/EP2019/062983, filed on May 20, 2019, which claims the benefit of European Patent Application No. 18175793.1, filed Jun. 4, 2018, the entire disclosures of which are hereby incorporated by reference for any and all purposes.

The present invention relates to preservation systems for use in consumer products.

BACKGROUND

The consumer goods industry has a constant need for agents having antimicrobial properties, in particular for the preservation of products which are otherwise perishable (such as e.g. cosmetics, pharmaceutical products or foodstuffs).

A large number of antimicrobial active compounds are already employed as preservation chemicals, but alternatives that avoid possible ecological concerns and are readily tolerated by the skin are required.

Such preservation systems should be stable, largely and preferably completely odourless, inexpensive to prepare, easy to formulate (i.e. preferably liquid) and should not be detrimental to the final product.

The present invention provides a particularly effective preservation system.

DESCRIPTION OF THE INVENTION

The present invention relates to an anti microbial preservation system comprising:
  i. itaconic acid or salt thereof and
  ii. an aromatic alcohol selected from the group consisting of ethylvanillin, eugenol, thymol, P-hydroxybenzaldehyde, 4n butyl phenol, P-hydroxyacetophenone, vanillin, salicylic acid or salt thereof, o-cymen-5-ol, carvacrol and mixtures thereof.

A second aspect of the invention relates to a composition comprising the antimicrobial preserving system described above.

A third aspect of the invention relates to a method of preserving a composition comprising the step of adding to the composition an antimicrobial preservation system comprising:
  i. itaconic acid or salt thereof and
  ii. an aromatic alcohol selected from the group consisting of ethylvanillin, eugenol, thymol, P-hydroxybenzaldehyde, 4n butyl phenol, P-hydroxyacetophenone, vanillin, salicylic acid or salt thereof, o-cymen-5-ol, carvacrol and mixtures thereof.

DETAILED DESCRIPTION OF THE INVENTION

The present invention relates to an antimicrobial preservation system comprising itaconic acid or salt thereof.

Preferably the acid form is used.

The preservation system further comprises an aromatic alcohol selected from the group consisting of ethylvanillin, eugenol, thymol, P-hydroxybenzaldehyde, 4n butyl phenol, P-hydroxyacetophenone, vanillin, salicylic acid or salt thereof, o-cymen-5-ol, carvacrol and mixtures thereof.

Preferred aromatic alcohols are ethylvanillin, eugenol, thymol, P-hydroxybenzaldehyde, 4n butyl phenol and mixtures thereof. Thymol and eugenol are more preferred, thymol being the most preferred.

Thymol may be added to the in purified form. Alternatively, thyme oil or thyme extract comprising thymol may be added to the preservation system. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide*, and *Thymus citriodorus*. The isomer of thymol (carvacrol) may also preferably be used.

It is preferred if the weight ratio of compound (C1 to C6), unsaturated, organic acid having at least two carboxyl groups to compound, preferably itaconic acid to aromatic alcohol, is from 1:50 to 50:1 more preferably from 1:10 to 10:1, most preferably from 1:5 to 5:1.

In a preferred embodiment of the invention the preserving system is included as part of a composition. Preferably the composition is a personal care composition and more preferably the composition is a hair treatment composition.

Preferably the total the level of preserving system within the composition is from 0.05 to 5 wt % of the total composition, more preferably from 0.2% to 2 wt % of the total composition.

The compositions of the invention, comprising the preserving system of the invention, preferably comprise at least 75 wt %, preferably at least 80 wt %, more preferably at least 85 wt % and most preferably at least 87 wt % of water, by weight of the total composition.

It is preferred if the composition further comprises cationic anionic, nonionic, zwitterionic or amphoteric surfactants or mixtures thereof.

Examples of suitable cationic surfactants which are useful include quaternary ammonium cationic surfactants corresponding to the following general formula:

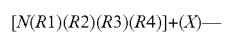

[N(R1)(R2)(R3)(R4)]+(X)— in which R1, R2, R3, and R4 are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such preferred quaternary ammonium cationic surfactants are cetyltrimethylammonium chloride (CTAC), behentrimonium chloride (BTAC) and mixtures thereof.

Alternatively, primary, secondary or tertiary fatty amines may be used in combination with an acid to provide a cationic surfactant suitable for use in the invention. The acid protonates the amine and forms an amine salt in situ. The amine is therefore effectively a non-permanent quaternary ammonium or pseudo-quaternary ammonium cationic surfactant.

Suitable fatty amines of this type include amidoamines of the following general formula:

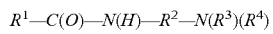

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms. Particularly preferred is stearamidopropyldimethylamine.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di-and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1 EO, 2EO and 3EO, ammonium lauryl sulphate and ammonium lauryl ether sulphate 1 EO, 2EO and 3EO.

Nonionic surfactants suitable for use in compositions of the invention may include condensation products of aliphatic (C8-C18) primary or secondary linear or branched chain alcohols or phenols with alkylene oxides, usually ethylene oxide and generally having from 6 to 30 ethylene oxide groups. Other suitable nonionics include mono-or di-alkyl alkanolamides, glycolipids preferably selected from the group of rhamnolipids and sophorolipids. Examples include coco mono-or di-ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

Generally, the surfactants are present in shampoo compositions of the invention in an amount of from 0.1 to 50%, preferably from 5 to 30%, more preferably from 8% to 20% by weight.

The invention will now be illustrated by the following non-limiting Examples

EXAMPLES

The differing behaviours of inhibitory antimicrobials in isolation and mixtures have been widely explored using the concept of the Fractional Concentration and Fractional Inhibitory Concentration (FIC). See for instance JRW Lambert and R Lambert, J. Appl. Microbiol 95, 734 (2003); T. Jadavji, CG Prober and R Cheung, Antimicrobial Agents and Chemotherapy 26, 91 (1984), and WO 2004/006876. These parameters can be defined as follows:

FC (component a)=Concentration of component a tested in the mixture/MIC (component a tested as a single active)

FIC (component a)=MIC (component a tested in the mixture)/MIC (component a tested as a single active)

The interactions between antimicrobials can be additive, synergistic or possibly antagonistic depending on whether the efficacy of the combination is equivalent to, greater than or less than that obtained for the same total concentration of the individual components when tested alone.

These relationships can be expressed mathematically by summing the fractional MIC values for all the components present in the mixture to give the "fractional inhibitory index":

$$\Sigma FIC = FIC_{(component\ 1)} + FIC_{(component\ 2)}$$

Such that:

$\Sigma FIC \geq 1$ corresponds to additive or antagonistic activity $\Sigma FIC < 1$ corresponds to synergistic activity A comparable method is the calculation of the synergy index (SI) which is an industrial accepted method described by Kull, F. C.; Eisman, P. C.; Sylwestrowicz, H. D. and Mayer, R. L., in Applied Microbiology 9:538-541 (1961).

METHODS

Liquid broth assays (MIC and checkerboard) were conducted to identify the minimum concentration(s) of individual and binary combinations of preservation chemicals. A modified methodology to ISO 20776-1:2006 was utilised for the screening as follows. Stock solutions of preservation chemicals and tryptic soy broth were inoculated with 1-5× $10^6$ microorganisms and incubated at 30° C. for 24 hours, after which optical densities at $OD_{600}$nm were measured. MIC was defined as the concentration at which <25% growth was observed in comparison to a positive growth control containing no preservation chemicals. Preservation chemicals were screened at a concentration range of 0.0156-2%.

TABLE 1

Microorganism pools
Microorganism pool

| Pool 1 | Gram negative non-fermenting bacteria: *Pseudomonas aeruginosa*, *Pseudomonas putida* & *Burkholderia cepacia* |
| Pool 2 | Gram negative fermenting bacteria: *Enterobacter gergoviae* & *Klebsiella* species |

TABLE 2

Chemical combination synergy scores

| | ΣFIC synergy score | | | |
|---|---|---|---|---|
| | Itaconic acid | | Citric Acid | |
| | Pool 1 | Pool 2 | Pool 1 | Pool 2 |
| Eugenol | 0.38 | 0.38 | 0.75 | 0.53 |
| Ethylvanillin | 0.56 | 0.63 | 0.63 | 0.69 |
| 4-n-butyl phenol | 0.44 | 0.50 | 0.50 | 0.59 |

The invention claimed is:

1. A hair-treatment composition comprising an antimicrobial preservation system and one or more surfactants; wherein the antimicrobial preservation system comprises:
   i. itaconic acid or salt thereof and
   ii. an aromatic alcohol selected from the group consisting of ethylvanillin, eugenol, thymol, and mixtures thereof;
   wherein a weight ratio of compound i) to compound ii) is from 1:10 to 50:1; and
      wherein the level of preservation system is from 0.05 to 5 wt % of the total composition;
   wherein the one or more surfactants comprises an amphoteric or a zwitterionic surfactant selected from the group consisting of alkyl betaines, alkyl amidopropyl betaines, alkyl sulphobetaines, alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms; and
   wherein the one or more surfactants are present in the hair-treatment composition in an amount of from 5% to 30% by weight.

2. The hair-treatment composition according to claim 1, wherein the aromatic alcohol is ethylvanillin and the weight ratio of itaconic acid to ethylvanillin is from 5:1 to 50:1.

3. The hair-treatment composition according to claim 1, wherein the aromatic alcohol is eugenol and the weight ratio of itaconic acid to eugenol is from 5:1 to 50:1.

4. The hair-treatment composition according to claim 1, wherein the aromatic alcohol is thymol and the weight ratio of itaconic acid to thymol is from 1:10 to 50:1.

5. The hair-treatment composition according to claim 1, wherein the composition is an aqueous.

6. The hair-treatment composition according to claim 5, comprising at least 75 wt % water, by weight of the total composition.

7. The hair-treatment composition according to claim 1, wherein the level of preservation system is from 0.05 to 2 wt % of the total composition.

8. The hair-treatment composition according to claim 1, wherein the level of preservation system is from 0.2 to 2 wt % of the total composition.

9. The hair-treatment composition according to claim 1, wherein the weight ratio of itaconic acid to aromatic alcohol is from 10:1 to 5:1.

10. The hair-treatment composition according to claim 1, wherein the composition is a shampoo composition.

11. The hair-treatment composition according to claim 1, wherein the amphoteric or a zwitterionic surfactant is selected from the group consisting of lauryl amine oxide, cocodimethyl sulphopropyl betaine, lauryl betaine, cocamidopropyl betaine and sodium cocamphopropionate.

* * * * *